US00PP20917P2

(12) United States Plant Patent
Hansoti

(10) Patent No.: US PP20,917 P2
(45) Date of Patent: Apr. 6, 2010

(54) ***TRADESCANTIA* PLANT NAMED 'SITARA GOLD'**

(50) Latin Name: *Tradescantia spathaceae nana*
Varietal Denomination: SITARA GOLD

(76) Inventor: Ashish Hansoti, 1, Navjivan Bldg, Dattatreya Road, Santa Cruz West, Mumbai, Maharashtra (IN) 400 054

( * ) Notice: Subject to any disclaimer, the term of this patent is extended or adjusted under 35 U.S.C. 154(b) by 0 days.

(21) Appl. No.: 12/221,436

(22) Filed: Aug. 2, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell

(57) ABSTRACT

A new and distinct *Tradescantia* cultivar named 'SITARA GOLD' is disclosed, characterized by very stable yellow foliage, and vigorous growth. The new variety is a *Tradescantia*, normally produced as an indoor potted plant, or as a tender outdoor landscape plant.

1 Drawing Sheet

Figure 1:
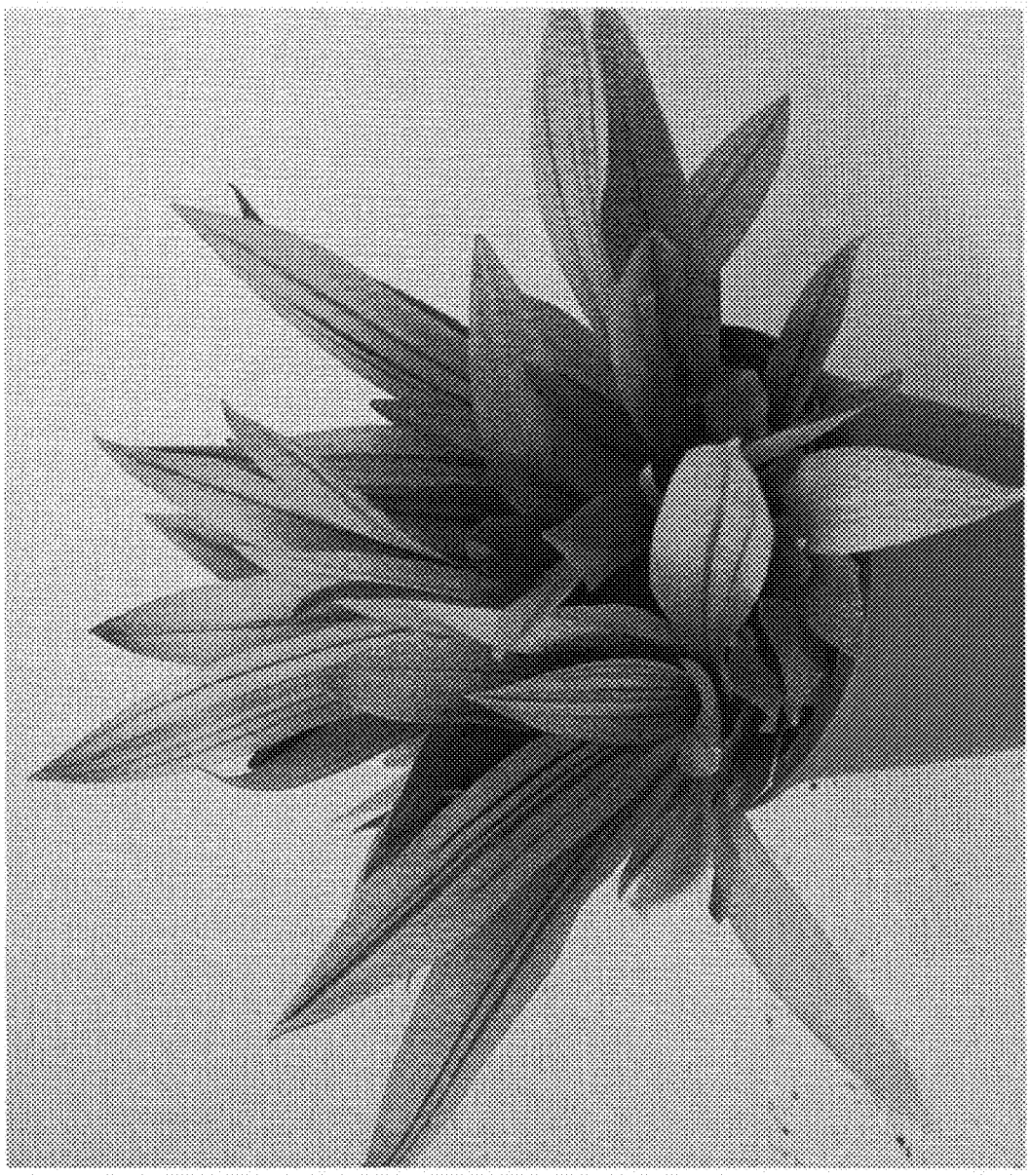

Latin name of the genus and species: *Tradescantia spathaceae nana.*

Variety denomination: 'SITARA GOLD'.

BACKGROUND OF THE INVENTION

The new cultivar is a product of a planned breeding program. The object of the breeding program was to select and reproduce *Tradescantia spathaceae nana* plants with brighter variegation of the leaves and improved plant forms. The new variety was discovered as a naturally occurring whole plant mutation in a grouping of more than 100 plants, of the parent variety, an unnamed, unpatented selection of *Tradescantia spathaceae nana*. The new variety was first noted as a whole plant mutation in January 2005. The new variety was discovered by Ashish Arvind Hansoti in January 2005 at a commercial greenhouse near Mumbai, India.

Asexual reproduction of the new cultivar 'SITARA GOLD' by vegetative tip cuttings was first performed at a commercial greenhouse outside of Mumbai, India in April of 2005 and has shown that the unique features of this cultivar are stable and reproduced true to type on successive generations. Approximately 12 generations have been reproduced.

SUMMARY OF THE INVENTION

The cultivar 'SITARA GOLD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SITARA GOLD' These characteristics in combination distinguish 'SITARA GOLD' as a new and distinct *Tradescantia* cultivar:

1. Exceptionally stable yellow foliage color.
2. Overall the plant is a slightly larger plant than the species *Tradescantia spathaceae nana.*
3. Despite its highly colored leaves, growth is vigorous and fills a commercial pot in a relatively short time frame.

Plants of the new cultivar 'SITARA GOLD' are similar to plants of the parent, *Tradescantia spathaceae nana* unnamed, unpatented selection, in most horticultural characteristics, however, plants of the new cultivar 'SITARA GOLD' are slightly larger. Additionally, the new variety has consistently bright yellow foliage, whereas the parent variety has inconsistent foliage color, which is primarily green.

The parent variety is the best commercial comparison to the new variety 'SITARA GOLD.'

BRIEF DESCRIPTION OF THE PHOTOGRAPH

The accompanying photograph in FIG. 1 illustrates in full color a typical plant of 'SITARA GOLD' grown in a greenhouse, in a 13cm pot. Age of the plant photographed is approximately 24 weeks The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SITARA GOLD' plants grown in a poly plastic covered greenhouse in Mumbai, India. The greenhouse is covered with an additional shade cloth, allowing 50% natural light through. The growing temperature ranged from 12° C. to 20° C. at night and 20° C. to 35° C. during the day. Light levels were approximately 30–35 LUX. Measurements and numerical values represent averages of typical plant types.

Botanical classification: *Tradescantia spathaceae nana* cultivar 'SITARA GOLD'.

PROPAGATION

Time to rooting: 20 days under summer conditions of approximately 25° C. to 40° C. 30 to 40 days under winter conditions of approximately 15° C. to 25° C.

Root description: Fleshy and fibrous roots. Free branching. New root tips are white but mature roots and root hairs are brown — somewhat lighter than N 199D.

PLANT

Growth habit: Herbaceous, upright tender perennial.
Height: Approximately 20 to 25 cm above a 13 cm pot.
Plant spread: Approximately 30 to 40 cm.
Growth rate: Rapid.
Branching characteristics: Forms clumps by lateral branching and suckers from fleshy stem and roots.
Length of lateral branches: Approximately 15 to 20 cm.
Diameter of lateral branches: Approximately 1 cm.
Quantity of lateral branches: Approximately 5 to 8 per main shoot
Color of lateral branches: Near RHS White 155C.
Lateral branch texture: Glabrous.
Branch strength: Brittle, succulent.
Number of leaves per lateral branch: Approximately 10 to 15.
Age of plant described: Approximately 22 weeks.

FOLIAGE

Leaf:

*Arrangement.*—Whorled.
*Average length.*—Approximately 18.8 cm.
*Average width.*—Approximately 2.8 cm.
*Shape of blade.*—Broadly linear.
*Apex.*—Acute.
*Base.*—Closed sheath.
*Attachment.*—Sessile.
*Margin.*—Entire.
*Texture of top surface.*—Smooth, waxy.
*Texture of bottom surface.*—Smooth.
*Leaf internode length.*—Approximately 0.5 cm, or less.
*Color.*—Young foliage upper side: Near RHS Yellow-Green 152D with lines of Green N138 A and Green 138B along length of leaf. Young foliage under side: Near RHS Greyed-Purple 186B with linear striations of Violet 86A. Mature foliage upper side: Near RHS Yellow-Green 153B with lines of Green N139A along length of leaf. Mature foliage under side: Near RHS Greyed-Purple 186A to 186B with lines of Violet 86A to 86B along length of leaf.
*Venation.*—Type: Linear. Venation color upper side: Between RHS Yellow-Green 153C and 153D. Venation color under side: Near RHS Greyed-Purple 186C.

FLOWER

Blooming not observed on the new cultivar.

OTHER CHARACTERISTICS

Disease resistance: Neither resistance nor susceptibility to diseases or pests has been observed in this variety.
Drought tolerance and cold tolerance: Tender perennial. Tolerates low temperatures to 6° C. without damage. Tolerant of high humidity and temperatures to 40° C., with shade. No drought tolerance has been observed.
Fruit/seed production: Not observed.

What is claimed is:

1. A new and distinct cultivar of *Tradescantia* plant named 'SITARA GOLD' as herein illustrated and described.

* * * * *